(12) United States Patent
Cramail et al.

(10) Patent No.: US 7,452,947 B2
(45) Date of Patent: Nov. 18, 2008

(54) SILICA-SUPPORTED POLYMERIZATION CATALYST

(75) Inventors: Henri Cramail, Sainte Terre (FR); Alain Deffieux, Bordeaux (FR); Cedric Dever, Talence (FR); Sergio Mastroianni, Martigues (FR)

(73) Assignee: BP Chemicals Limited, Middlesex (GB)

( * ) Notice: Subject to any disclaimer, the term of this patent is extended or adjusted under 35 U.S.C. 154(b) by 627 days.

(21) Appl. No.: 10/524,435

(22) PCT Filed: Aug. 14, 2003

(86) PCT No.: PCT/GB03/03570

§ 371 (c)(1),
(2), (4) Date: Feb. 15, 2005

(87) PCT Pub. No.: WO2004/018523

PCT Pub. Date: Mar. 4, 2004

(65) Prior Publication Data

US 2006/0153763 A1 Jul. 13, 2006

(30) Foreign Application Priority Data

Aug. 20, 2002 (EP) .................. 02358016
Mar. 3, 2003 (EP) .................. 03358004

(51) Int. Cl.
*C08F 4/42* (2006.01)

(52) U.S. Cl. .................... 526/128; 526/125.3; 526/158; 526/351; 526/352; 502/103; 502/152; 502/158

(58) Field of Classification Search .................. 526/160, 526/943, 351, 352, 125.3, 128, 158; 502/103, 502/152, 158
See application file for complete search history.

(56) References Cited

OTHER PUBLICATIONS dos Santos et al., "Indenyl-Silica Xerogels: New Materials for Supporting Metallocene Catalysts", Applied Catalysis A: General, vol. 220, 287-302 (2001).*
dos Santos et al., "I::thylene (co)polymerization with Supported-Metallocenes Prepared by the Sol-Gel Method", Polymer, vol. 42, 4517-4525 (2001).*
Hay et al., "A Versatile Route to Organically-Modified Silicas and Porous Silicas via the Non-Hydrolytic Sol-Gel Process", Journal of Materials Chemistry, vol. 10, 1811-1818 (2000).*
Dos Santos, J. H. Z. et al., "Indenyl-Silica Xerogels: New Materials for Supporting Metallocene Catalysts", Applied Catalysis A: General, vol. 220, pp. 287-302, (2001).
Dos Santos, J. H. Z. et al., "Ethylene (co)polymerization with Supported-Metallocenes Prepared by the Sol-Gel Method", Polymer, vol. 42, pp. 4517-4525, (2001).
Apperley, D. et al., "Silica-Dimethylsiloxane Hybrids-Non-Hydrolytic Sol-Gel Synthesis and Characterization by NMR Spectroscopy", Chem. Mater., vol. 14, No. 3, pp. 983-988, (2002).
Hay, J. N. et al., "Synthesis of Organic-Inorganic Hybrids via the Non-Hydrolytic Sol-Gel Process", Chem. Mater., vol. 13, No. 10, pp. 3396-3403, (2001).
Hay, J. N. et al., "A Versatile Route to Organically-Modified Silicas and Porous Silicas via the Non-Hydrolytic Sol-Gel Process", Journal of Materials Chemistry, vol. 10, No., pp. 1811-1818, (2000).

* cited by examiner

*Primary Examiner*—Ling-Siu Choi
(74) *Attorney, Agent, or Firm*—Finnegan, Henderson, Farabow, Garrett & Dunner, L.L.P.

(57) ABSTRACT

A process for the preparation of a silicon containing transition metal compound that includes the steps of (a) non-hydrolytic sol-gel condensation of a silane of formula $L_xSiQ_n$ wherein L is a σ-bonded ligand, Q is an anionic ligand, and $x+n=4$ with a halogenated silane (or siloxane) and an alkoxysilane, (b) optionally alkylation, (c) deprotonation and (d) addition of a transition metal compound. The process allows for the preparation of transition metal compounds which may suitably be used with cocatalysts for the polymerization of olefins, in particular for such processes carried out in the gas phase.

13 Claims, No Drawings

SILICA-SUPPORTED POLYMERIZATION CATALYST

CROSS REFERENCE TO RELATED APPLICATIONS

This application is a National Phase Application based on PCT/GB2003/003570, filed Aug. 14, 2003, and claims the priority of European Patent Application Nos. 02358016.0, filed Aug. 20, 2002, and 03358004.4, filed Mar. 3, 2003, all of which are incorporated herein by reference in their entirety.

BACKGROUND OF THE INVENTION

The present invention relates to the preparation of polymerisation catalysts, and in particular to the preparation of silicon containing transition metal catalyst components for use in the polymerisation of olefins.

In recent years there have been many advances in the production of polyolefin homopolymers and copolymers due to the introduction of metallocene catalysts. Metallocene catalysts offer the advantage of generally a higher activity than traditional Ziegler catalysts and are usually described as catalysts which are single site in nature.

There have been developed several different families of metallocene complexes. In earlier years catalysts based on bis (cyclopentadienyl) metal complexes were developed, examples of which may be found in EP 129368 or EP 206794. More recently complexes having a single or mono cyclopentadienyl ring have been developed. Such complexes have been referred to as 'constrained geometry' complexes and examples of these complexes may be found in EP 416815 or EP 420436. In both of these complexes the metal atom eg. zirconium is in the highest oxidation state.

Other complexes however have been developed in which the metal atom may be in a reduced oxidation state. Examples of both the bis (cyclopentadienyl) and mono (cyclopentadienyl) complexes have been described in WO 96/04290 and WO 95/00526 respectively.

The above metallocene complexes are utilised for polymerisation in the presence of a cocatalyst or activator. Typically activators are aluminoxanes, in particular methyl aluminoxane or compounds based on boron compounds. Examples of the latter are borates such as trialkyl-substituted ammonium tetraphenyl- or tetrafluorophenylborates. Catalyst systems incorporating such borate activators are described in EP 561479, EP 418044 and EP 551277.

The above metallocene complexes may be used for the polymerisation of olefins in solution, slurry or gas phase. When used in the slurry or gas phase the metallocene complex and/or the activator are suitably supported. Typical supports include inorganic oxides eg. silica or polymeric supports may alternatively be used.

Examples of the preparation of supported metallocene catalysts for the polymerisation of olefins may be found in WO 94/26793, WO 95/07939, WO 96/00245, WO 96/04318, WO 97/02297 and EP 642536.

Supported metallocene catalysts may be prepared by use of sol-gel techniques.

Silicate gels are typically prepared by hydrolyzing monomeric tetrafunctional alkoxide precursors utilizing a mineral acid or base as a catalyst. For example the hydrolysis and condensation of tetraethoxysilane in a sol-gel process catalysed by ammonia results in a sol-gel powder which may be used as an organometallic catalyst support.

In *J. Applied Polymer Science* Vol. 78, 2318-2326 (2000) there is described silica supports for metallocenes prepared by the gelation of a stable colloidal phase of silica using $MgCl_2$ as initiator. *Polymer Bulletin* 46, 175-182 (2001) describes the synthesis of metallocene catalysts supported on silica type sol-gel carriers. The silica gels were prepared in a wet sol-gel procedure by hydrolysis and condensation of tetraethoxysilane in a mixture of water, ethyl alcohol and ammonia.

*Polymer* 42, 2001 pgs 4517-4525 describes the preparation of supported metallocenes by use of xerogels based on the hydroylsis and condensation reactions between tetraethoxysilane and bis(indenyl)diethoxysilane. In all the above preparations the resultant supported catalysts were employed in the polymerisation of ethylene.

*Applied Catalysis* 230, Pg. 287-302 (2001) describes indenyl-silica xerogels prepared by hydrolysis and polycondensation of bis(indenyl)diethoxysilanes and tetraethoxysilane.

SUMMARY OF THE INVENTION

We have now surprisingly found that sol-gel techniques which utilise a non-hydrolytic procedure may be successfully used in the preparation of silicon containing transition metal compound for the polymerisation of olefins.

Thus according to the present invention there is provided a process for the preparation of a silicon containing transition metal compound, said process comprising the steps of (a) non-hydrolytic sol-gel condensation of a silane of formula

$$L_xSiQ_n$$

wherein L is a σ-bonded ligand,

Q is an anionic ligand, and x+n=4 with an halogenated silane (or siloxane) and an alkoxysilane, (b) optionally alkylation, (c) deprotonation, and (d) addition of a transition metal compound.

DETAILED DESCRIPTION OF THE INVENTION

L is typically a cyclopentadienyl, indenyl or fluorenyl ligand.

Q is typically a halogen ligand and in particular is chloride

Preferred silanes are bis(cyclopentadienyl) dihalogenated silanes or bis(indenyl)cyclopentadienyl dihalogenated silanes.

The (cyclopentadienyl) dihalogenated silane is typically a dichlorinated compound.

The preferred dihalogenated silanes are those having one or two cyclopentadienyl ligands however bis(cyclopentadienyl) compounds for example bis(cyclopentadienyl)dichlorosilanes or bis(indenyl)dichlorosilanes are most preferred.

The preferred alkoxysilanes are ethoxysilanes for example tetraethoxysilane.

The preferred halogenated silanes are chlorosilanes for example tetrachlorosilane or dimethyldichlorosilane.

Suitable halogenated siloxanes for step (a) include for example dichlorotetramethylsiloxanes.

The non-hydrolytic condensation in step (a) is performed in the presence of a condensation catalyst for example a transition metal compound. A most suitable condensation catalyst is zirconium tetrachloride.

The non-hydrolytic sol-gel condensation has the advantage of allowing the reaction in step (a) to take place without solvent and under mild conditions The alkylation step, when present, may be carried out by use of well known passivation agents, for example triethylaluminium.

The deprotonation step may be carried out by use of well known deprotonation agents for example n-butyllithium.

The sol-gel condensation products of the present invention may be represented by the following structure:

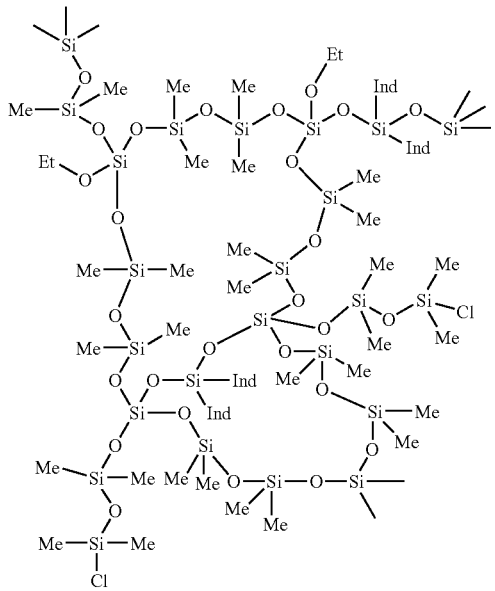

The transition metal compound used in step (d) is typically a Group IVA metal compound for example zirconium, titanium or hafnium metal compound and is preferably a halogenated compound. Preferred compounds are zirconium tetrachloride or titanium tetrachloride.

Other suitable Group IVA metal compounds for use in the present invention include metal amines for example $Zr(NMe_2)_4$ or similar. The use of a transition metal amine in step (d) has the advantage of grafting the metal directly on the sol-gel thereby avoiding the need for the specific deprotonation agent.

The process according to the present invention may additionally include a final halogenation step for example addition of chlorotrimethylsilane thereby forming the metal dichloride species. This is particularly the case when $Zr(NMe_2)_4$ or similar are used.

Thus according to another aspect of the present invention there is provided a process for the preparation of a silicon containing transition metal compound, said process comprising the steps of (a) non-hydrolytic sol-gel condensation of a silane of formula $$L_xSiQ_n$$

wherein L is a σ-bonded ligand,

Q is an anionic ligand x+n=4 with an halogenated silane (or siloxane) and an alkoxysilane, (b) alkylation, and (c) addition of a transition metal amine.

The process of the present invention is particularly suitable for the preparation of silicon containing metallocene catalyst components which may contain either a single σ-bonded ligand or two σ-bonded ligands.

The transition metal compound may be used for the polymerisation of olefins in the presence of any suitable activator component well known for use with transition metal catalysts.

These include aluminoxanes such as methyl aluminoxane (MAO), boranes such as tris(pentafluorophenyl)borane and borates.

Aluminoxanes are well known in the art and preferably comprise oligomeric linear and/or cyclic alkyl aluminoxanes. Aluminoxanes may be prepared in a number of ways and preferably are prepared by contacting water and a trialkylaluminium compound, for example trimethylaluminium, in a suitable organic medium such as benzene or an aliphatic hydrocarbon.

A preferred aluminoxane is methyl aluminoxane (MAO).

Other suitable cocatalysts are organoboron compounds in particular triarylboron compounds. A particularly preferred triarylboron compound is tris(pentafluorophenyl) borane.

Other compounds suitable as cocatalysts are compounds which comprise a cation and an anion. The cation is typically a Bronsted acid capable of donating a proton and the anion is typically a compatible non-coordinating bulky species capable of stabilizing the cation.

Such cocatalysts may be represented by the formula:

$$(L^*-H)^+_d(A^{d-})$$

wherein $L^*$ is a neutral Lewis base $(L^*-H)^+_d$ is a Bronsted acid $A^{d-}$ is a non-coordinating compatible anion having a charge of $d^-$, and d is an integer from 1 to 3.

The cation of the ionic compound may be selected from the group consisting of acidic cations, carbonium cations, sylium cations, oxonium cations, organometallic cations and cationic oxidizing agents.

Suitably preferred cations include trihydrocarbyl substituted ammonium cations eg. triethylammonium, tripropylammonium, tri(n-butyl)ammonium and similar. Also suitable are N.N-dialkylanilinium cations such as N,N-dimethylanilinium cations.

The preferred ionic compounds used as cocatalysts are those wherein the cation of the ionic compound comprises a hydrocarbyl substituted ammonium salt and the anion comprises an aryl substituted borate.

Typical borates suitable as ionic compounds include:
triethylammonium tetraphenylborate
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
N,N-dimethylanilinium tetrakis(pentafluorophenyl) borate,
N,N-diethylanilinium tetrakis(pentafluorphenyl) borate.

Another type of cocatalyst suitable for use with the transition metal catalyst components of the present invention comprise ionic compounds comprising a cation and an anion wherein the anion has at least one substituent comprising a moiety having an active hydrogen.

Suitable cocatalysts of this type are described in WO 98/27119 the relevant portions of which are incorporated herein by reference.

Thus according to another aspect of the present invention there is provided a catalyst system for the polymerisation of olefins comprising (a) a transition metal compound as hereinbefore described and (b) a cocatalyst.

The transition metal catalysts of the present invention may be suitable for the polymerisation of olefin monomers selected from (a) ethylene, (b) propylene (c) mixtures of ethylene and propylene and (d) mixtures of (a), (b) or (c) with one or more other alpha-olefins.

Thus according to another aspect of the present invention there is provided a process for the polymerisation of olefin monomers selected from (a) ethylene, (b) propylene (c) mixtures of ethylene and propylene and (d) mixtures of (a), (b) or (c) with one or more other alpha-olefins, said process performed in the presence of a silicon containing transition metal catalyst system as hereinbefore described.

Particularly preferred polymerisation processes are those comprising the polymerisation of ethylene or the copolymerisation of ethylene and α-olefins having from 3 to 10 carbon atoms.

The transition metal catalysts of the present invention may be used for the polymerisation of olefins in either the solution, slurry or gas phase.

A slurry process typically uses an inert hydrocarbon diluent and temperatures from about 0° C. up to a temperature just below the temperature at which the resulting polymer becomes substantially soluble in the inert polymerisation medium. Suitable diluents include toluene or alkanes such as hexane, propane or isobutane. Preferred temperatures are from about 30° C. up to about 200° C. but preferably from about 60° C. to 100° C. Loop reactors are widely used in slurry polymerisation processes.

The preferred process for the present invention is the gas phase.

Suitable gas phase processes of the present invention include the polymerisation of olefins, especially for the homopolymerisation and the copolymerisation of ethylene and α-olefins for example 1-butene, 1-hexene, 4-methyl-1-pentene are well known in the art. Particularly preferred gas phase processes are those operating in a fluidised bed. Examples of such processes are described in EP 89691 and EP 699213 the latter being a particularly preferred process for use with the supported catalysts of the present invention.

The present invention will be further described by reference to the following examples:

EXAMPLE 1

Preparation of Support No: 1

In a glove box, zirconium tetrachloride (0.18 mmol) and bis(indenyl)dichlorosilane* (1.01 mmol) were introduced into a Schlenk tube. The tube was connected to a vacuum/$N_2$ line and dimethyldichlorosilane (4.51 mmol) and tetraethoxysilane (2.83 mmol) were successively added via syringes. The mixture was stirred for 5 minutes and transferred via a syringe to another tube which was then sealed under vacuum. The sealed tube was introduced in a steel envelope and held in an oven at 110-115° C. After 8 days the tube was opened in a glove box under $N_2$ and the resultant gel dried under vacuum at room temperature for 6 hrs. The chemical composition of the gel was as follows:

| | Elemental Analysis | | | | | |
|---|---|---|---|---|---|---|
| | C | H | Cl | Si | Zr | O |
| Mass % | 31.96 | 5.34 | 2.36 | 30.75 | 1.4 | 28.19 |

These results indicate a final structure of:

$SiZr_{0.02}O_{1.36}(OEt)_{0.0.3}Cl_{0.03}Ind_{0.2}Me_{1.1}$.

NB. * prepared according to Organometallics 1993, 12, 4607-4612.

EXAMPLE 2

Preparation of Metallocene Catalyst Component A 1.94 mmol of n-butyl lithium was added dropwise at room temperature to 163 mg. of Support No: 1, prepared in example 1, in suspension of pentane (nBuLi/Indenyl=5.5). The reaction mixture was kept under reflux for 7 hrs. The solvent was removed under vacuum and the solid washed with 3 aliquots of 8 ml. pentane and then dried under vacuum at room temperature for 1 hr.

To the suspension of the resulting solid in 10 ml tetrahydofuran, 0.177 mmol $ZrCl_4.2THF$ in tetrahydrofuran were added dropwise at room temperature. The mixture was then stirred for 1 hr. The resultant solid was then filtered, washed with 2 aliquots of 10 ml. tetrahydrofuran and dried under vacuum.

EXAMPLE 3

Polymerisation of Component A

In a Schlenk tube were introduced 6.8 mg. of the metallocene catalyst component A, prepared in example 2, (6.3 μmol $Ind_2ZrCl_2$), 50 ml toluene and 4.2 ml of methyl aluminoxane (Al/Zr=1000). After stirring for 10 min. the system was degassed. The mixture was held at 60° C. and a continuous flow of ethylene (pressure=1 bar) was maintained. After 1 hr. the polymerisation was terminated by adding acidic ethanol. The precipitated polymer was filtered and dried under vacuum for 8 hr. at room temperature. 1.01 g. of polyethylene was obtained corresponding to an activity of 110 $gPE/(g_{catalyst}.h..bar)$.

The polymer was characterised as having Mn=44800, Mw=124100 and MWD=2.8.

EXAMPLE 4

Preparation of Support No: 2

In a glove box, zirconium tetrachloride (0.352 mmol) and bis(indenyl)dichlorosilane* (3.01 mmol) were introduced into a Schlenk tube. The tube was connected to a vacuum/$N_2$ line and dichlorotetramethylsiloxane (5.093 mmol) and tetraethoxysilane (4.403 mmol) were successively added via syringes. The mixture was stirred for 5 minutes and transferred via a syringe to another tube which was then sealed under vacuum. The sealed tube was introduced in a steel envelope and held in an oven at 110-115° C. After 8 days the tube was opened in a glove box under $N_2$ and the resultant gel dried under vacuum at room temperature for 6 hrs. The chemical composition of the gel was as follows:

| Elemental Analysis | | | | | |
|---|---|---|---|---|---|
| | C | H | Cl | Si | Zr | O |
| Mass % | 44.71 | 5.79 | 5.35 | 24.75 | 1.61 | 17.79 |

These results indicate a final structure of:

$SiZr_{0.02}O_{1.12}(OEt)_{0.11}Cl_{0.11}Ind_{0.34}Me_{1.16}$.

NB. * prepared according to Organometallics 1993, 12, 4607-4612.

EXAMPLE 5

Preparation of Metallocene Catalyst Component B

A suspension of Support No: 2 (120 mg corresponding to 1.12 mmol of Si) in pentane was reacted with triethylaluminium (TEA) (0.67 mmol). The mixture was kept stirring for 6 hours. After stopping the stirring and waiting for the decantation, the supernatant liquid was removed by the use of a canula. The resulting solid was washed with pentane in the same manner and dried under vacuum 1.91 mmol of n-butyl lithium was added dropwise at room temperature to a suspension of the passivated solid in pentane (nBuLi/Indenyl=5). The reaction mixture was kept under reflux overnight. After stopping the stirring and waiting for the decantation, the supernatant liquid was removed by the use of a canula. The solid was washed with pentane in the same manner and dried under vacuum.

To the suspension of the resulting solid in tetrahydofuran, 0.191 mmol $ZrCl_4.2THF$ in tetrahydrofuran were added dropwise at room temperature. The mixture was then stirred for 1 hr. The solvent was eliminated by vacuum, pentane was added, the suspension was kept stirring for 1 h. After stopping the stirring and waiting for the decantation, the supernatant liquid was removed by the use of a canula. The solid was dried under vacuum.

EXAMPLE 6

Polymerisation of Component B

In a Schlenk tube were introduced 3.9 mg of the metallocene catalyst component A, prepared in example 5, (4.9 µmol $Ind_2ZrCl_2$), 50 ml toluene and 3.2 ml of methyl aluminoxane (Al/Zr=1000). After stirring for 10 min. the system was degassed. The mixture was held at 60° C. and a continuous flow of ethylene (pressure=1 bar) was maintained. After 1 hr. the polymerisation was terminated by adding acidic ethanol. The precipitated polymer was filtered and dried under vacuum for 8 hr. at room temperature. 0.74 g. of polyethylene was obtained corresponding to an activity of 190 gPE/($g_{catalyst}$.h..bar).

The polymer was characterised as having Mn=8700, Mw=168400 and MWD=19.

EXAMPLE 7

Preparation of Support No: 3

In a glove box, zirconium tetrachloride (0.417 mmol) and bis(indenyl)dichlorosilane* (2.1 mmol) were introduced into a Schlenk tube. The tube was connected to a vacuum/$N_2$ line and dichlorotetramethylsiloxane (6.913 mmol) and tetraethoxysilane (4.923 mmol) were successively added via syringes. The mixture was stirred for 5 minutes and transferred via a syringe to another tube which was then sealed under vacuum. The sealed tube was introduced in a steel envelope and held in an oven at 110-115° C. After 11 days the tube was opened in a glove box under $N_2$ and the resultant gel dried under vacuum at room temperature for 6 hrs. The chemical composition of the gel was as follows:

| Elemental Analysis | | | |
|---|---|---|---|
| | C | H | Cl |
| Mass % | 39.28 | 6.00 | 3.97 |

These results indicate a final structure of:

$SiZr_{0.02}O_{1.17}(OEt)_{0.11}Cl_{0.11}Ind_{0.2}Me_{1.33}$.

NB. * prepared according to Organometallics 1993, 12, 4607-4612.

EXAMPLE 8

Preparation of Metallocene Catalyst Component C

A suspension of Support No: 3 (145.4 mg corresponding to 1.58 mmol of Si) in pentane was reacted with triethylaluminium (TEA) (0.98 mmol). The mixture was kept stirring for 20 hours. After stopping the stirring and waiting for the decantation, the supernatant liquid was removed by the use of a canula. The resulting solid was washed with pentane in the same manner and dried under vacuum.

0.16 mmol of $Zr(NMe_2)_4$ was added at room temperature to support No. 3 ($Zr(NMe_2)_4$/Indenyl=0.5). Toluene was added and the reaction was stirred overnight at 100° C. The solvent was removed via reduced pressure. Pentane and chlorotrimethylsilane (3.2 mmol) were then added and the reaction was stirred overnight at room temperature. After stopping the stirring and waiting for the decantation, the supernatant liquid was removed by the use of a canula. The solid was washed with THF and pentane in the same manner and dried under vacuum.

EXAMPLE 9

Polymerisation of Component C

In a Schlenk tube were introduced 6 mg. of the metallocene catalyst component C (corresponding to a theoretical amount of 5.5 µmol $Ind_2ZrCl_2$), 50 ml toluene and methyl aluminoxane (Al/Zr=1000). After stirring for 10 min. the system was degassed. The mixture was held at 60° C. and a continuous flow of ethylene (pressure=1 bar) was maintained. After 1 hr. the polymerisation was terminated by adding acidic ethanol. The precipitated polymer was filtered and dried under vacuum for 8 hr. at room temperature. 0.327 g. of polyethylene was obtained corresponding to an activity of 65 gPE/($g_{catalyst}$.h.bar).

The polymer was characterised as having Mw=317 kg/mol and MWD=45.

What is claimed is:
1. A process for the preparation of a silicon containing transition metal catalyst compound, said process comprising the steps of
   (a) non-hydrolytic sol-gel condensation of (i) a silane of formula

$L_xSiQ_n$ wherein L is a σ-bonded ligand, Q is an anionic ligand, and x+n=4 with (ii) a halogenated silane or a haloqenated siloxane and (iii) an alkoxysilane,
 (b) optionally alkylation,
 (c) deprotonation, and
 (d) addition of a transition metal compound.

2. A process according to claim 1, wherein L is a cyclopentadienyl, indenyl or fluorenyl ligand.

3. A process according to claim 1, wherein x is 2 and Q is halogen.

4. A process according to claim 1, wherein the transition metal compound is a Group IV A metal halide.

5. A process according to claim 4, wherein the Group IV A metal is zirconium.

6. A process for the preparation of a silicon containing transition metal catalyst compound, said process comprising the steps of
 (a) non-hydrolytic sol-gel condensation of (i) a silane of formula $$L_xSiQ_n$$

wherein L is a σ-bonded ligand, Q is an anionic ligand, and x+n=4 with (ii) a halogenated silane or a halo,qenated siloxane and (iii) an alkoxysilane,
 (b) alkylation, and
 (c) addition of a transition metal amine.

7. A process according to claim 6, wherein the transition-metal amine is $Zr(NMe_2)_4$.

8. A polymerisation catalyst system comprising (a) a silicon containing transition metal catalyst compound prepared according to claim 1, and (b) a cocatalyst.

9. A process for the polymerisation of olefin monomers selected from (a) ethylene, (b) propylene (c) mixtures of ethylene and propylene and (d) mixtures of (a), (b) or (c) with one or more other alpha-olefins, said process being performed in the presence of a silicon containing transition metal catalyst compound prepared according to claim 1, and (b) cocatalyst.

10. A process for the polymerisation of ethylene or the copolymerization of ethylene and α-olefins having from 3 to 10 carbon atoms, said process being carried out in the presence of a (a) a silicon containing transition metal catalyst compound prepared according to claim 1, and (b) a cocatalyst.

11. A process according to claim 9 or 10, wherein the cocatalyst is an aluminoxane.

12. A process according to claim 9 or 10, wherein the cocatalyst has the formula:

$$(L^*-H)^+_d(A^{d-})$$

wherein
 $L^*$ is a neutral Lewis base
 $(L^*-H)^+_d$ is a Bronsted acid
 $A^{d-}$ is a non-coordinating compatible anion having a charge of d−, and
 d is an integer from 1 to 3.

13. A process according to claim 9 or 10, carried out in the gas phase.

* * * * *